United States Patent
Niwa et al.

(10) Patent No.: US 10,703,697 B2
(45) Date of Patent: Jul. 7, 2020

(54) METHOD FOR REFINING ORGANIC COMPOUND

(71) Applicant: NGK INSULATORS, LTD., Nagoya (JP)

(72) Inventors: Kousuke Niwa, Niwa-Gun (JP); Hiroaki Isobe, Nagoya (JP)

(73) Assignee: NGK Insulators, Ltd., Nagoya (JP)

(*) Notice: Subject to any disclaimer, the term of this patent is extended or adjusted under 35 U.S.C. 154(b) by 0 days.

(21) Appl. No.: 16/275,547

(22) Filed: Feb. 14, 2019

(65) Prior Publication Data

US 2019/0194101 A1 Jun. 27, 2019

Related U.S. Application Data

(63) Continuation of application No. PCT/JP2017/029450, filed on Aug. 16, 2017.

(30) Foreign Application Priority Data

Aug. 19, 2016 (JP) .................................. 2016-161435

(51) Int. Cl.
*B01J 19/12* (2006.01)
*C07C 29/80* (2006.01)
(Continued)

(52) U.S. Cl.
CPC ............. *C07C 29/80* (2013.01); *B01D 1/0029* (2013.01); *B01D 1/30* (2013.01); *B01D 9/005* (2013.01);
(Continued)

(58) Field of Classification Search
CPC ......... B01J 19/12; B01J 19/128; C07C 29/80; C07C 31/04; C07B 63/00; B01D 17/005;
(Continued)

(56) References Cited

U.S. PATENT DOCUMENTS

2009/0127478 A1 5/2009 Inoue et al.

FOREIGN PATENT DOCUMENTS

EP 0 541 114 A2 5/1993
JP 2709260 B2 * 2/1998 ............. B32B 29/00
(Continued)

OTHER PUBLICATIONS

English translation of International Preliminary Report on Patentability (Chapter I) (Application No. PCT/JP2017/029450) dated Feb. 28, 2019, 8 pages.

(Continued)

*Primary Examiner* — Cameron J Allen
(74) *Attorney, Agent, or Firm* — Burr & Brown, PLLC (57) ABSTRACT

An organic compound refinement method for refining a specific organic compound which is a target compound from at least two types of organic compounds. The method includes separating the target compound from an organic compound other than the target compound while the at least two types of organic compounds are irradiated with light at an infrared absorption wavelength of a specific functional group that is not contained in the target compound but is contained in the organic compound other than the target compound, or separating the target compound from an organic compound other than the target compound while the at least two types of organic compounds are irradiated with light at an infrared absorption wavelength of a specific functional group that is contained in the target compound but is not contained in the organic compound other than the target compound.

7 Claims, 3 Drawing Sheets

(51) Int. Cl.
- *C07B 63/00* (2006.01)
- *C07C 31/04* (2006.01)
- *B01D 1/00* (2006.01)
- *B01D 1/30* (2006.01)
- *B01D 9/00* (2006.01)
- *B01D 15/38* (2006.01)
- *B01D 17/00* (2006.01)

(52) U.S. Cl.
CPC ....... *B01D 15/3804* (2013.01); *B01D 17/005* (2013.01); *B01J 19/12* (2013.01); *B01J 19/128* (2013.01); *C07B 63/00* (2013.01); *C07C 31/04* (2013.01); *B01D 2221/10* (2013.01)

(58) Field of Classification Search
CPC ........ B01D 9/005; B01D 1/30; B01D 1/0029; B01D 15/3804; B01D 2221/10
See application file for complete search history.

(56) References Cited

FOREIGN PATENT DOCUMENTS

| | | |
|---|---|---|
| JP | 2010-150086 A | 7/2010 |
| JP | 2011-213640 A | 10/2011 |
| JP | 2014-189462 A | 10/2014 |
| JP | 2017-050254 A | 3/2017 |
| WO | 2007/052778 A1 | 5/2007 |
| WO | 2015-140062 A1 | 9/2015 |

OTHER PUBLICATIONS

Atsushi Sakurai, "Thermal Radiation Control by Metamaterial," National Heat Transfer Symposium of Japan Koen Ronbunshu, 2014, vol. 51, H344.

International Search Report and Written Opinion (Application No. PCT/JP2017/029450) dated Oct. 3, 2017.

European Search Report, European Application No. 17841527.9, dated Apr. 2, 2020 (7 pages).

* cited by examiner

METHOD FOR REFINING ORGANIC COMPOUND

BACKGROUND OF THE INVENTION

1. Field of the Invention

The present invention relates to a method for refining an organic compound.

2. Description of the Related Art

Commonly known methods for refining a target organic compound include distillation, recrystallization, chromatography, and extraction. PTL 1 discloses a method for refining an organic compound using laser light. In PTL 1, when a material in a metastable form is selectively produced from a solution containing the material that forms stable and metastable crystals, the solution is irradiated with a laser beam to generate air bubbles, and metastable crystal nuclei are thereby generated, so that the metastable crystals are selectively produced.

CITATION LIST

Patent Literature

PTL 1: Japanese Unexamined Patent Application Publication No. 2014-189462

SUMMARY OF THE INVENTION

However, the method described in PTL 1 is a method for selectively producing a metastable crystalline material, is not widely applicable to methods for refining organic compounds, and disadvantageously lacks versatility. In PTL 1, the solution is irradiated with the laser light in order to generate air bubbles in the solution, and no attention is paid to light at an infrared absorption wavelength of the material.

The present invention has been made to solve the foregoing problem, and it is a principal object to provide a highly versatile method for refining a target organic compound with higher purity in a simpler manner than with conventional methods.

The organic compound refinement method of the present invention is a method for refining a specific organic compound which is a target compound from at least two types of organic compounds, the method including separating the target compound from an organic compound other than the target compound while the at least two types of organic compounds are irradiated with light at an infrared absorption wavelength of a specific functional group that is not contained in the target compound but is contained in the organic compound other than the target compound, or separating the target compound from an organic compound other than the target compound while the at least two types of organic compounds are irradiated with light at an infrared absorption wavelength of a specific functional group that is contained in the target compound but is not contained in the organic compound other than the target compound.

In the former refinement method, the at least two types of organic compounds are irradiated with the light at the infrared absorption wavelength of the specific functional group not contained in the target compound but contained in the organic compound other than the target compound. In this case, since energy is selectively given to the organic compound other than the target compound among the at least two types of organic compounds, the organic compound is vaporized at a temperature lower than its normal boiling point, resists crystallization because of its increased thermal motion, or has reduced affinity for a stationary phase used in chromatography. By utilizing the change in characteristics, the target compound can be isolated from the organic compound other than the target compound with higher purity in a simpler manner than with conventional methods. This method is applicable to refinement of various organic compounds and is highly versatile.

In the latter refinement method, the at least two types of organic compounds are irradiated with the light at the infrared absorption wavelength of the specific functional group contained in the target compound but not contained in the organic compound other than the target compound. In this case, since energy is selectively given to the target compound, the target compound is vaporized at a temperature lower than its normal boiling point, resists crystallization because of its increased thermal motion, or has reduced affinity for a stationary phase used in chromatography. By utilizing the change in characteristics, the target compound can be isolated from the organic compound other than the target compound with higher purity in a simpler manner than with conventional methods. This method is applicable to refinement of various organic compounds and is highly versatile.

Examples of the separation method include distillation, recrystallization, chromatography, and extraction. The organic compounds used in the present invention may be low-molecular weight compounds or may be high-molecular weight compounds. The high-molecular weight compounds may be natural products such as proteins or artificial products such as synthetic resins. The recrystallization encompasses selective recrystallization of a compound having a specific structure (e.g., a method for selectively crystallizing only specific crystals of a compound that exhibits crystal polymorphism).

DETAILED DESCRIPTION OF THE INVENTION

A preferred embodiment of the present invention will next be described.

A first refinement method in the present embodiment is a method for refining a specific organic compound which is a target compound from at least two types of organic compounds. The method includes separating the target compound from a compound other than the target compound while the at least two types of organic compounds are irradiated with light at an infrared absorption wavelength of a specific functional group that is not contained in the target compound but is contained in the organic compound other than the target compound.

A second refinement method in the present embodiment is a method for refining a specific organic compound which is a target compound from at least two types of organic compounds. The method includes separating the target compound from a compound other than the target compound while the at least two types of organic compounds are irradiated with light at an infrared absorption wavelength of a specific functional group that is contained in the target compound but is not contained in the organic compound other than the target compound.

A description will be given of the case in which, for example, a component A is separated from a solution mixture containing a target compound (the component A) and an organic compound (the component B) other than the target compound. It is assumed that both the components A and B form crystals.

Figure 1A:
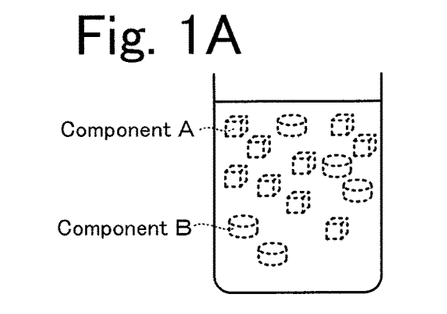
FIGS. 1A-1B show illustrations of an example of a first refinement method.
Figure 1B:
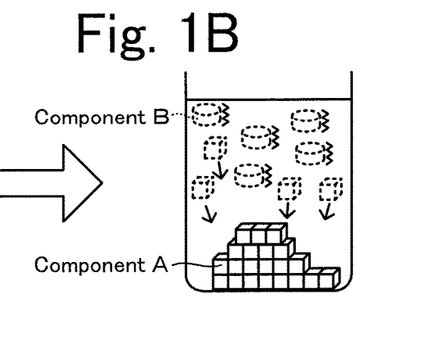

When the component A is recrystallized directly from the solution mixture, the recrystallization is performed while the solution mixture containing the components A and B dissolved therein (see FIG. 1A) is irradiated with light at an infrared absorption wavelength of a specific functional group that is not contained in the component A but is contained in the component B (see FIG. 1B, the first refinement method). In FIGS. 1A-1B, dissolved components are indicated by dotted lines, and a crystallized component is indicated by solid lines. The thermal motion of molecules of the component B is assumed to be more vigorous when the component B is irradiated with the light at the infrared absorption wavelength than when the component B is not irradiated. Therefore, as the solution containing the components A and B dissolved therein is cooled in the course of recrystallization, the component A whose molecules are not undergoing vigorous thermal motion is first crystallized, and crystallization of the component B whose molecules are undergoing vigorous thermal motion is suppressed. In this case, the number of recrystallization operations necessary to obtain the component A with high purity can be lower than in conventional methods.

Figure 2A:
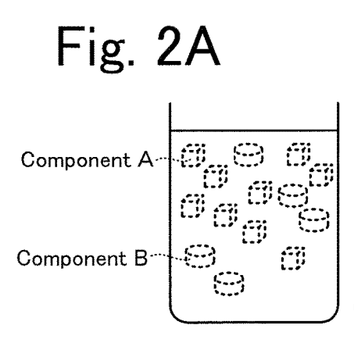
FIGS. 2A-2D show illustrations of an example of a second refinement method.
Figure 2B:
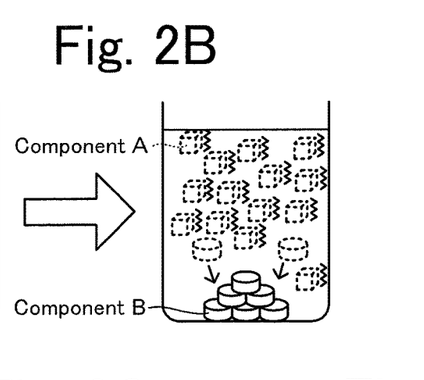
Figure 2C:
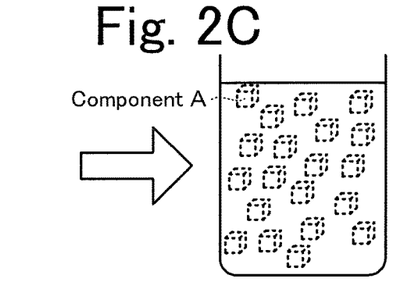
Figure 2D:
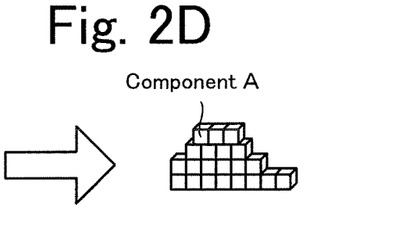

When the component A is collected after the concentration of the component A in the solution mixture is increased, recrystallization is performed while the solution mixture containing the components A and B dissolved therein (see FIG. 2A) is irradiated with light at an infrared absorption wavelength of a specific functional group that is contained in the component A but is not contained in the component B (see FIG. 2B, the second refinement method). In FIGS. 2A-2B also, dissolved components are indicated by dotted lines, and a crystallized component is indicated by solid lines. The thermal motion of the molecules of the component A is assumed to be more vigorous when the component A is irradiated with the light at the infrared absorption wavelength than when the component A is not irradiated. Therefore, as the solution containing the components A and B dissolved therein is cooled in the course of recrystallization, the component B whose molecules are not undergoing vigorous thermal motion is first crystallized, and crystallization of the component A whose molecules are undergoing vigorous thermal motion is suppressed. Then the crystallized component B is removed by filtration, and a filtrate containing the component A at a high concentration is thereby obtained (see FIG. 2C). Then the solvent in the filtrate is removed by evaporation, and the component A can thereby be obtained with high purity (see FIG. 2D). Instead of removing the solvent in the filtrate by evaporation, the component A may be recrystallized from the filtrate.

Next, a description will be given of the case in which the component A is separated from the solution mixture containing the target compound (the component A) and the organic compound (the component B) other than the target compound by distillation.

When the boiling point of the component B is lower than the boiling point of the component A, the distillation is performed while the solution mixture is irradiated with light at an infrared absorption wavelength of a specific functional group that is not contained in the component A but is contained in the component B (the first refinement method). Vaporization of the component B proceeds at around its normal boiling point when the component B is not irradiated with the light at the infrared absorption wavelength. However, when the component B is irradiated with the light at the infrared absorption wavelength, the energy state of the component B increases, and therefore the vaporization of the component B may proceed at a temperature lower than its normal boiling point. However, since the energy state of the component A is unchanged irrespective of whether the component A is irradiated with the light at the infrared absorption wavelength, vaporization of the component A proceeds at its normal boiling point irrespective of whether the component A is irradiated. Therefore, when the distillation is performed under irradiation with the light at the infrared absorption wavelength, the difference in boiling point between the component A and the component B increases, and they can be separated from each other with high accuracy.

When the boiling point of the component A is lower than the boiling point of the component B, the distillation is performed while the solution mixture is irradiated with light at an infrared absorption wavelength of a specific functional group that is contained in the component A but is not contained in the component B (the second refinement method). Vaporization of the component A proceeds at around its normal boiling point when the component A is not irradiated with the light at the infrared absorption wavelength. However, when the component A is irradiated with the light at the infrared absorption wavelength, the energy state of the component A increases, and therefore the vaporization of the component A may proceed at a temperature lower than its normal boiling point. However, since the energy state of the component B is unchanged irrespective of whether the component B is irradiated with the light at the infrared absorption wavelength, vaporization of the component B proceeds at its normal boiling point irrespective of whether the component B is irradiated. Therefore, when the distillation is performed under irradiation with the light at the infrared absorption wavelength, the difference in boiling point between the component A and the component B increases, and they can be separated from each other with high accuracy.

A description will be given of a specific method for selectively collecting, for example, methanol from a methanol-water solution mixture efficiently. When the methanol-water solution mixture is irradiated only with infrared light of about 2,700 to about 3,000 $cm^{-1}$ at which O—H stretching vibrations of water do not occur but O—H stretching vibrations, C—H stretching vibrations, or C—H deformation vibration of methanol occur, only methanol absorbs infrared energy selectively. Therefore, the vaporization of methanol proceeds at a lower temperature in a shorter time than when the mixture is not irradiated with the infrared light and is heated and distilled using a conventional method, and the methanol and water can thereby be separated from each other. When the methanol-water solution mixture is irradiated only with infrared light in a wavenumber range in which absorption of the infrared light by methanol does not occur and which is selected from about 3,200 to about 3,600 cm$^{-1}$ where O—H stretching vibrations occur or with infrared light of about 1,600 to about 1,800 cm$^{-1}$ where O—H deformation vibrations occur, only water absorbs infrared energy selectively. Therefore, the vaporization of water proceeds at a lower temperature in a shorter time than when the mixture is not irradiated with the infrared light and is heated and distilled using a conventional method, and the methanol and water can thereby be separated from each other.

Next, a description will be given of the case in which the component A is separated from the solution mixture containing the target compound (the component A) and the organic compound (the component B) other than the target compound by column chromatography.

When the elution time of the component B is shorter than the elution time of the component A, the components A and B, together with the mobile phase, are caused to pass through the stationary phase while the stationary phase in the column is irradiated with light at an infrared absorption wavelength of a specific functional group that is not contained in the component A but is contained in the component B (the first refinement method). Since the affinity of the component B for the stationary phase when the component B is irradiated with the light at the infrared absorption wavelength can be considered to be lower than when the component B is not irradiated, the component B is eluted faster. However, since the affinity of the component A for the stationary phase does not change irrespective of whether the component A is irradiated with the light at the infrared absorption wavelength, the elution time of the component A is unchanged irrespective of whether the component A is irradiated. Therefore, when the component A and the component B are separated from each other by column chromatography under irradiation with the light at the infrared absorption wavelength, the difference in elution time between the component A and the component B increases, and they can be separated from each other with high accuracy.

When the elution time of the component A is shorter than the elution time of the component B, the components A and B, together with the mobile phase, are caused to pass through the stationary phase while the stationary phase in the column is irradiated with light at an infrared absorption wavelength of a specific functional group that is contained in the component A but is not contained in the component B (the second refinement method). Since the affinity of the component A for the stationary phase when the component A is irradiated with the light at the infrared absorption wavelength can be considered to be lower than when the component A is not irradiated, the component A is eluted faster. However, since the affinity of the component B for the stationary phase does not change irrespective of whether the component B is irradiated with the light at the infrared absorption wavelength, the elution time of the component B is unchanged irrespective of whether the component B is irradiated. Therefore, when the component A and the component B are separated from each other by column chromatography under irradiation with the light at the infrared absorption wavelength, the difference in elution time between the component A and the component B increases, and they can be separated from each other with high accuracy.

When, for example, the component A is an alcohol compound having no ketone group and the component B is a ketone compound having no hydroxy group, the specific functional group that is not contained in the component A but is contained in the component B may be a ketone group, and the solution mixture may be irradiated with light at the infrared absorption wavelength of C=O stretching vibrations. The specific functional group that is contained in the component A but is not contained in the component B may be a hydroxy group, and the solution mixture may be irradiated with light at the infrared absorption wavelength of O—H stretching vibrations, C—O stretching vibrations, or O—H deformation vibrations.

Moreover, the above-described principle is applicable to a compound that exhibits crystal polymorphism that is the ability of molecules of the compound in the form of crystals to have different molecular arrangements, and only a specific crystal structure can be obtained. The crystal polymorphism is important for solid pharmaceuticals, and different polymorphic crystal structures differ in solubility, bioavailability, and stability. The reason that the crystal polymorphism occurs is that, when crystals precipitate from a solution, their crystallization occurs in different energy states. Therefore, for example, under irradiation with infrared light that is absorbed only by an unnecessary crystal structure and is selected from infrared absorption spectra specific to expected crystal structures, the target crystal structure can be selectively crystallized and can be obtained at a higher yield in a simpler manner than with conventional methods.

In the refinement methods in the present embodiment, during irradiation with light at an infrared absorption wavelength of a specific functional group, it is preferable to use an infrared heater that emits infrared radiation having a peak at a target wavelength from a structural member including a metal pattern, a dielectric layer, and a metal substrate that are stacked in this order from the outside toward the inside.

Figure 3:
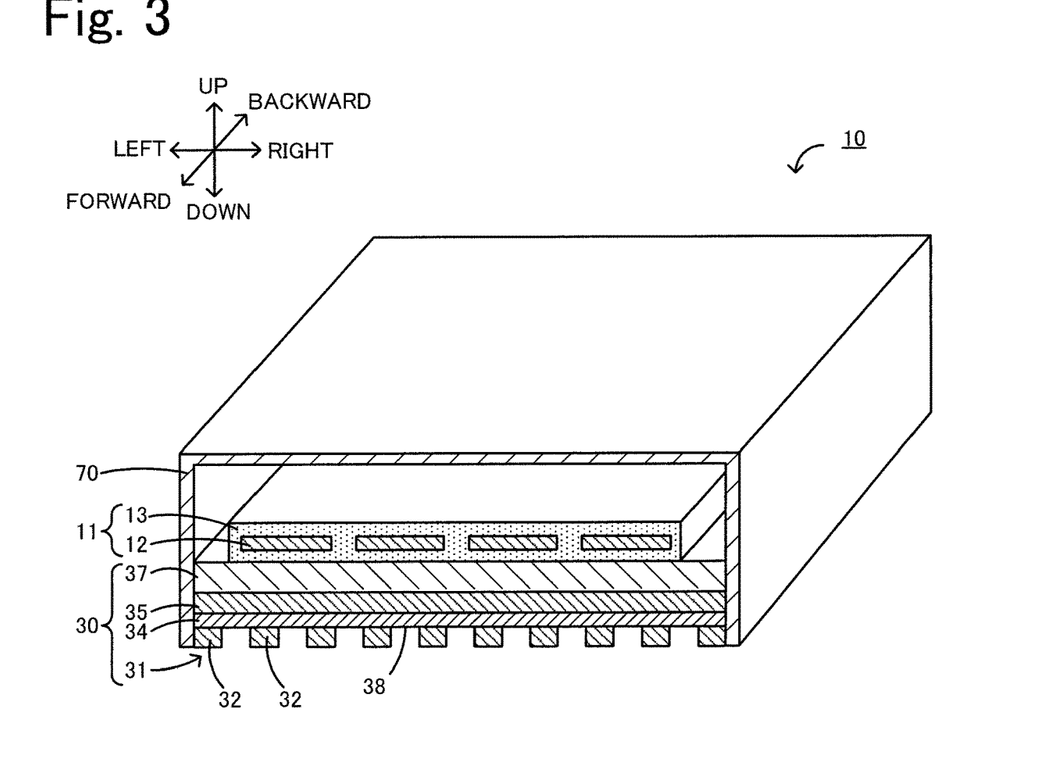
FIG. 3 is a perspective view of an infrared heater 10.
Figure 4:
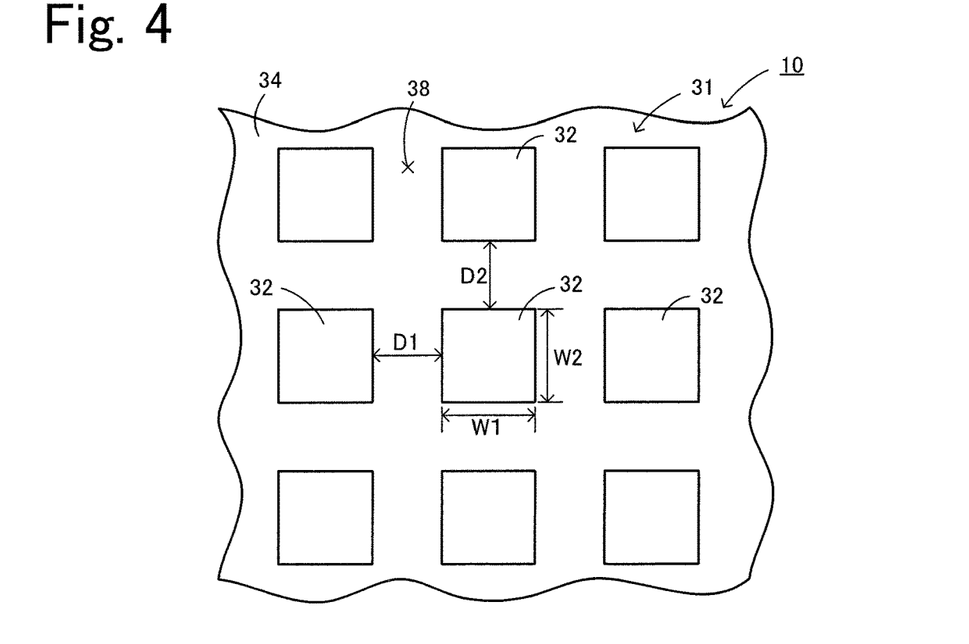
FIG. 4 is a partial bottom view of the infrared heater 10.

FIG. 3 is a perspective view, partially in cross section, of the infrared heater 10. FIG. 4 is a partial bottom view of the infrared heater 10. Left and right directions, front and rear directions, and upward and downward directions are as shown in FIG. 3. The infrared heater 10 includes a heater main body 11, a structural member 30, and a casing 70. The infrared heater 10 emits infrared radiation toward an unillustrated target disposed below the infrared heater 10.

The heater main body 11 is formed as a so-called planer heater and includes: a heating element 12 prepared by bending a linear member into a zigzag pattern; and a protective member 13 that is in contact with the heating element 12 and surrounds the heating element 12. Examples of the material of the heating element 12 include W, Mo, Ta, Fe—Cr—Al alloys, and Ni—Cr alloys. Examples of the material of the protective member 13 include insulating resins such as polyimide and ceramics. The heater main body 11 is disposed inside the casing 70. Opposite ends of the heating element 12 are connected a pair of unillustrated input terminals attached to the casing 70. Electric power can be supplied from the outside to the heating element 12 through the pair of input terminals. The heater main body 11 may be a planar heater having a structure including an insulating member and a ribbon-shaped heating element wound around the insulating member.

The structural member 30 is a plate-shaped member disposed below the heating element 12. The structural member 30 includes a first conductor layer 31, a dielectric layer 34, a second conductor layer 35, and a support substrate 37 that are stacked in this order from the outer lower side of the infrared heater 10 toward its inner side. The structural member 30 is disposed so as to block a lower opening of the casing 70.

As shown in FIG. 4, the first conductor layer 31 is formed as a metal pattern having a periodic structure including metal electrodes 32 having the same shape and the same size and arranged at regular intervals on the dielectric layer 34. Specifically, the first conductor layer 31 is formed as the metal pattern including a plurality of quadrangular metal electrodes 32 disposed on the dielectric layer 34 at regular intervals D1 in the left-right direction and at regular intervals D2 in the front-rear direction. The metal electrodes 32 each have a shape having a thickness (a vertical height) smaller than its lateral width W1 (the width in the left-right direction) and its longitudinal width W2 (the width in the front-rear direction). The lateral period of the metal pattern is $\Lambda 1=D1+W1$, and its longitudinal period is $\Lambda 2=D2+W2$. It is assumed that D is equal to D2 and W1 is equal to W2. Examples of the material of the metal electrodes 32 include gold and aluminum (Al). The metal electrodes 32 are joined to the dielectric layer 34 through an unillustrated bonding layer. Examples of the material of the bonding layer include chromium (Cr), titanium (Ti), and ruthenium (Ru).

The dielectric layer 34 is a plate-shaped member having an upper surface joined to the second conductor layer 35. The dielectric layer 34 is held between the first conductor layer 31 and the second conductor layer 35. A portion of the lower surface of the dielectric layer 34 on which portion no metal electrodes 32 are disposed serves as an emission surface 38 that emits infrared radiation toward a target. Examples of the material of the dielectric layer 34 include alumina ($Al_2O_3$) and silica ($SiO_2$).

The second conductor layer 35 is a metal plate having an upper surface joined to the support substrate 37 through an unillustrated bonding layer. The material of the second conductor layer 35 may be the same as the material of the first conductor layer 31. Examples of the material of the bonding layer include chromium (Cr), titanium (Ti), and ruthenium (Ru).

The support substrate 37 is a plate-shaped member fixed inside the casing 70 with an unillustrated fixture and supports the first conductor layer 31, the dielectric layer 34, and the second conductor layer 35. Examples of the material of the support substrate 37 include materials such as Si wafers and glass that can easily maintain a smooth surface, have high heat resistance, and resist heat warpage. The support substrate 37 may be in contact with the lower surface of the heater main body 11 or may not be in contact with the heater main body 11 and may be disposed so as to be vertically separated from the heater main body 11 with a space therebetween. When the support substrate 37 is in contact with the heater main body 11, they may be joined together.

This structural member 30 functions as a metamaterial emitter having the characteristic that infrared radiation having a specific wavelength is selectively emitted. This characteristic is considered to be due to a resonance phenomenon described by magnetic polaritons. The magnetic polaritons means a resonance phenomenon in which a strong electromagnetic wave confinement effect is obtained in a dielectric (the dielectric layer 34) between two upper and lower conductors (the first conductor layer 31 and the second conductor layer 35). Therefore, in the structural member 30, portions of the dielectric layer 34 that are held between the second conductor layer 35 and the metal electrodes 32 serve as infrared emission sources. The infrared radiation emitted from the emission sources travels along the metal electrodes 32 and is then emitted to the ambient environment through the portion of the dielectric layer 34 on which no metal electrodes 32 are disposed (i.e., the emission surface 38). In the structural member 30, the resonance wavelength can be controlled by adjusting the materials of the first conductor layer 31, the dielectric layer 34, and the second conductor layer 35 and the shape and periodic structure of the first conductor layer 31. Therefore, the infrared radiation emitted from the emission surface 38 of the structural member 30 has the characteristic that the emissivity of infrared radiation is high at a specific wavelength. In the present embodiment, the materials, the shape, and the periodic structure described above are adjusted such that the structural member 30 has the characteristic that infrared radiation having a maximum peak with a half-width of 1.5 μm or less (preferably 1.0 μm or less) and an emissivity of 0.7 or more (preferably 0.8 or more) in a wavelength range of from 0.9 μm to 25 μm inclusive (preferably from 2.5 μm to 25 μm inclusive (4000 to 400 $cm^{-1}$)) is emitted from the emission surface 38 (this characteristic is hereinafter referred to simple as a "prescribed emission characteristic"). Specifically, the structural member 30 has the characteristic that infrared radiation having a steep maximum peak with a relatively small half-width and a relatively large emissivity is emitted.

The structural member 30 can be produced, for example, as follows. First, a bonding layer (not shown) and the second conductor layer 35 are formed in this order on a surface (the lower surface in FIG. 3) of the support substrate 37 by sputtering. Next, the dielectric layer 34 is formed on a surface (the lower surface in FIG. 3) of the second conductor layer 35 by an ALD method (atomic layer deposition method). Then a prescribed resist pattern is formed on a surface (the lower surface in FIG. 3) of the dielectric layer 34, and a bonding layer (not shown) and a layer made of the material of the first conductor layer 31 are sequentially formed by a helicon sputtering method. Then the resist pattern is removed, and the first conductor layer 31 (the plurality of metal electrodes 32) is thereby formed.

The casing 70 has a substantially cuboidal shape having an inner space and an open bottom. The heater main body 11 and the structural member 30 are disposed in the inner space of the casing 70. The casing 70 is made of a metal (e.g., SUS or aluminum) so that the infrared radiation emitted from the heating element 12 is reflected.

An example of the use of the infrared heater 10 will be described. First, electric power is supplied from an unillustrated power source to the opposite ends of the heating element 12 through the input terminals. The electric power is supplied such that the temperature of the heating element 12 reaches a preset temperature (350° C. in this case, but the temperature is not particularly limited to 350° C.). Energy is transferred from the heating element 12 heated to the preset temperature to its surroundings through at least one of three forms of heat transfer, i.e., conduction, convection and radiation, and the structural member 30 is thereby heated. Therefore, the structural member 30 is heated to a prescribed temperature, serves as a secondary radiator, and emits infrared radiation. In this case, since the structural member 30 includes the first conductor layer 31, the dielectric layer 34, and the second conductor layer 35 as described above, the infrared heater 10 emits infrared radiation based on the prescribed emission characteristic.

Figure 5:
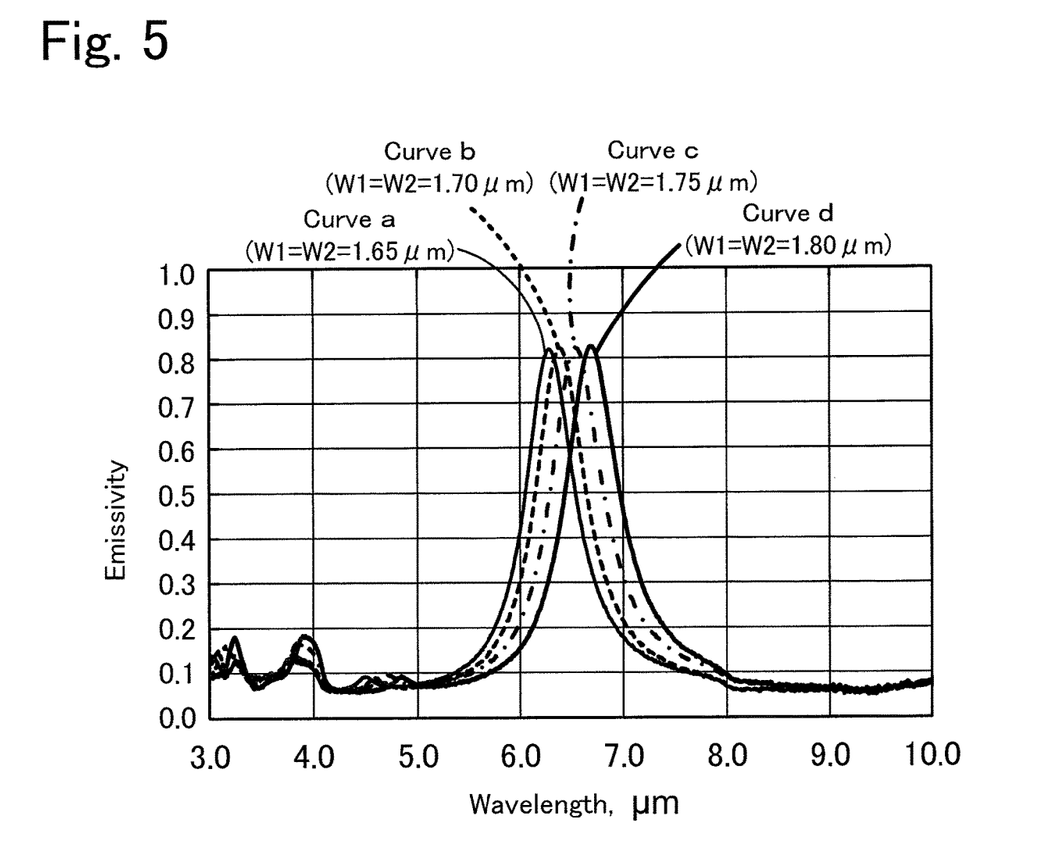
FIG. 5 is a graph showing examples of the emission characteristic of infrared radiation emitted from an emission surface 38.

FIG. 5 is a graph showing examples of the emission characteristic of the infrared radiation emitted from the emission surface 38. Curves a to d shown in the graph in FIG. 5 show measurements of the emissivity of the infrared radiation emitted from the emission surface 38 when different lateral widths W1 and different longitudinal widths W2 of the metal electrodes 32 were used. The emissivity was measured as follows. First, the normal incidence hemispherical reflectance for the infrared radiation from the emission surface 38 was measured using an FT-IR (Fourier transform infrared spectrometer) having an integrating sphere. Next, values converted using the formula (emissivity)=1−(reflectance), i.e., the Kirchhoffs law with the transmittance set to 0, were used as the measurements of the emissivity. The curves a to d each show the results obtained by using gold for the first conductor layer 31 and the second conductor layer 35, using alumina for the dielectric layer 34, setting the thickness of the first conductor layer 31 to 100 μm, setting the intervals D1 and the intervals D2 to 1.50 μm, setting the thickness of the dielectric layer 34 to 120 μm, and setting the temperature of the structural member 30 to 200° C. The curve a (the thin solid line), the curve b (the broken line), the curve c (the dash-dot line), and the curve d (the thick solid line) in the graph show the results when the lateral width W1 (=the longitudinal width W2) was set to 1.65 μm, 1.70 μm, 1.75 μm, and 1.80 μm, respectively. In all the curves a to d, the half-width of the maximum peak was 1.5 μm or less, more specifically 1.0 μm or less, and the emissivity of the maximum peak was larger than 0.7 (=70%), more specifically larger than 0.8 (=80%). As can be seen, as the width of the metal electrodes 32 increases from 1.65 μm to 1.85 μm, the peak wavelength (resonance wavelength) shifts to the long wavelength side. Table 1 shows the computation values and measurement values of the peak wavelength. Theoretically predicted values of the resonance wavelength using an LC circuit model were used as the computational values. As can be seen in Table 1, the computational values agree reasonably well with the measurement values. The width of the metal electrodes 32 formed was changed in increments of 0.05 μm, and the peak wavelength was changed in increments of several tenths of micrometers. Therefore, the peak wavelength can be adjusted to the target wavelength with high accuracy. It is expected that, when the metal electrodes 32 are designed such that their width is changed in increments of 0.01 μm, the peak wavelength can be changed in increments of several tens of nanometers. In this case, the peak wavelength can be adjusted to the target wavelength more accurately.

TABLE 1

| Width of metal electrodes W1 (=W2) [μm] | Peak wavelength(Resonance wavelength) | |
| --- | --- | --- |
| | Computation values λ LC | Measurement values λ exp |
| 1.65 | 6.13 μm (1631 cm$^{-1}$) | 6.29 μm (1590 cm$^{-1}$) |
| 1.70 | 6.32 μm (1582 cm$^{-1}$) | 6.39 μm (1565 cm$^{-1}$) |
| 1.75 | 6.50 μm (1538 cm$^{-1}$) | 6.54 μm (1529 cm$^{-1}$) |
| 1.80 | 6.69 μm (1495 cm$^{-1}$) | 6.69 μm (1495 cm$^{-1}$) |

The infrared heater 10 described above is designed so as to emit mainly infrared radiation having the target wavelength. However, it is difficult to completely remove radiation components other than the radiation component having the target wavelength in the infrared radiation from the structural member 30. In the atmosphere, heat dissipation from components of the heater to its surroundings by convection is expected to occur. Therefore, when an actual process is designed, various considerations should be given to the shape of the apparatus etc. in order to prevent an excessive increase in the temperature of raw materials etc. caused by the associated heat flow.

In the first refinement method in the present embodiment described above in detail, since energy is selectively given to the organic compound other than the target compound among the at least two types of organic compounds, the organic compound is vaporized at a temperature lower than its normal boiling point, resists crystallization because of its increased thermal motion, or has reduced affinity for the stationary phase used for chromatography. By utilizing the change in characteristics, the target compound can be isolated from the organic compound other than the target compound with higher purity in a simpler manner than with conventional methods.

In the second refinement method in the present embodiment, since energy is selectively given to the target compound, the target compound is vaporized at a temperature lower than its normal boiling point, resists crystallization because of its increased thermal motion, or has reduced affinity for the stationary phase used for chromatography. By utilizing the change in characteristics, the target compound can be isolated from the organic compound other than the target compound with higher purity in a simpler manner than with conventional methods.

Moreover, the infrared heater 10 used emits infrared radiation having a peak at a specific wavelength from the structural member 30 that has absorbed energy from the heating element 12. The infrared heater 10 can be designed such that the peak wavelength of the infrared radiation emitted matches the target wavelength (of light at an infrared absorption wavelength of a specific functional group) with high accuracy.

Moreover, the first conductor layer 31 is formed as a metal pattern having a periodic structure including the metal electrodes 32 having the same shape and the same size and arranged at regular intervals. In the infrared heater 10, the peak wavelength of the infrared radiation emitted varies with the lateral width W1 and the longitudinal width W2 of the metal electrodes 32. The lateral width W1 and the longitudinal width W2 of the metal electrodes 32 produced can be adjusted to their design values with high accuracy by, for example, lithography and liftoff using a well-known electron-beam lithography system. Therefore, the peak wavelength of the infrared radiation emitted from the infrared heater 10 can be adjusted to the target wavelength relatively easily with high accuracy.

The target wavelength is set within the wavelength range of from 0.9 μm to 25 μm inclusive (preferably a wavelength of from 2.5 μm to 25 μm inclusive (4,000 to 400 cm$^{-1}$)), and this wavelength range covers the measurement range of an ordinary infrared absorption spectrum.

It is needless to say that the present invention is not limited to the above-described embodiment, and that the present invention can be implemented in other various embodiments insofar as falling within the technical scope of the invention.

For example, in the above embodiment, the refinement methods exemplified include recrystallization, distillation, and column chromatography, but the refinement methods are not particularly limited to these methods. For example, the refinement method of the present invention may be applied to extraction.

In the above embodiment, the metal electrodes 32 have a quadrangular shape, but this is not a limitation. For example, the metal electrodes 32 may have a circular shape or a cross shape (a shape including perpendicularly intersecting rectangles). When the metal electrodes 32 are circular, the diameter of the circle corresponds to the lateral width W1 and the longitudinal width W2. When the metal electrodes 32 have a cross shape, the lengths of the long sides of the two intersecting rectangles correspond to the lateral width W1 and the longitudinal width W2. The metal electrodes 32 are arranged in a lattice pattern at regular intervals in the left-right direction and the front-rear direction, but this is not a limitation. For example, the metal electrodes 32 may be arranged at regular intervals only in the left-right direction or the front-rear direction.

In the above embodiment, the structural member 30 includes the support substrate 37, but the support substrate 37 may be omitted. In the structural member 30, the first conductor layer 31 and the dielectric layer 34 may be directly joined together with no bonding layer therebetween. The second conductor layer 35 and the support substrate 37 may be directly joined together with no bonding layer therebetween.

EXAMPLES

Example 1

A distillation apparatus was charged with 500 mL of a 50 vol % aqueous methanol solution and boiling chips, and distillation was performed at normal pressure. The distillation apparatus was heated to 85° C., and a flask containing the aqueous methanol solution in the distillation apparatus was irradiated from above with infrared radiation of 2,950 to 3,050 cm$^{-1}$ having a peak at 3,000 cm$^{-1}$ (5 W, area irradiated with infrared radiation: 3 cm square/irradiation energy per unit area: about 0.5 W/cm$^2$). While the irradiation was continued, a distillation procedure was conducted. The amount of the distilled solution (a concentrated methanol solution) was measured 5 minutes, 10 minutes, and 20 minutes after the start of the distillation. The wavelength range of the infrared radiation used for irradiation corresponds to a wavelength range in which C—H stretching vibrations or C—H deformation vibration of methanol occur. The results are shown in Table 2.

Example 2

In the infrared irradiation conditions in Example 1, the infrared radiation used for irradiation was changed to infrared radiation of 1,030 to 1,130 cm$^{-1}$ having a peak at 1,080 cm$^{-1}$ (5 W, area irradiated with infrared radiation: 3 cm square/irradiation energy per unit area: about 0.5 W/cm$^2$). The amount of the distilled solution (a concentrated methanol solution) was measured 5 minutes, 10 minutes, and 20 minutes after the start of the distillation. The wavelength range of the infrared radiation used for irradiation corresponds to a wavelength range in which C—O stretching vibrations of methanol occur.
The results are shown in Table 2.

Comparative Example 1

A distillation apparatus was charged with 500 mL of a 50 vol % aqueous methanol solution and boiling chips, and distillation was performed at normal pressure. The distillation apparatus was heated to 85° C., and the amount of the distilled solution (a concentrated methanol solution) was measured 5 minutes, 10 minutes, and 20 minutes after the start of the distillation. The results are shown in Table 2.

TABLE 2

| Passage of time from the start of distillation (minutes) | Amount of distilled solution (mL) | | |
|---|---|---|---|
| | Example 1 | Example 2 | Comparative Example 1 |
| 5 | 20 | 27 | 12 |
| 10 | 47 | 65 | 31 |
| 20 | 101 | 140 | 70 |

In Example 1, irradiation with infrared radiation of 2,950 to 3,050 cm$^{-1}$ having a peak at 3,000 cm$^{-1}$ was performed. In Example 2, irradiation with infrared radiation of 1,030 to 1,130 cm$^{-1}$ having a peak at 1,080 cm$^{-1}$ was performed. In Comparative Example 1, irradiation with infrared radiation was not performed. As can be seen from Table 2, the distillation proceeded faster in Examples 1 and 2. The results show that by performing distillation under irradiation with infrared radiation in an infrared absorption wavelength range of methanol, the distilled solution can be obtained at a faster speed than when no irradiation is performed. The concentration of methanol in the distilled solutions was 80 to 85%.

Example 3

A distillation apparatus was charged with 500 mL of a 50 vol % aqueous methanol solution and boiling chips, and distillation was performed at normal pressure. The distillation apparatus was heated to 35° C., and a flask containing the aqueous methanol solution in the distillation apparatus was irradiated from above with infrared radiation of 1,650 to 1,750 cm$^{-1}$ having a peak at 1,700 cm$^{-1}$ (5 W, area irradiated with infrared radiation: 3 cm square/irradiation energy per unit area: about 0.5 W/cm$^2$). While the irradiation was continued, a distillation procedure was conducted. The amount of the distilled solution was measured 5 minutes, 10 minutes, and 20 minutes after the start of the distillation. The composition of the distilled solution was confirmed to be almost 100% water (95 vol % or more). The wavelength range of the infrared radiation used for irradiation corresponds to a wavelength range in which H—O—H stretching vibrations of water occur. The results are shown in Table 3.

Comparative Example 2

A distillation apparatus was charged with 500 mL of a 50 vol % aqueous methanol solution and boiling chips, and distillation was performed at normal pressure. The distillation apparatus was heated to 35° C., and the state of distillation was checked 10 minutes, 30 minutes, and 60 minutes after the start of the distillation. However, the progress of the distillation was not found.

TABLE 3

| Passage of time from the start of distillation (minutes) | Amount of distilled solution (mL) | |
|---|---|---|
| | Example 3 | Comparative Example 2 |
| 10 | 3 | — |
| 30 | 12 | — |
| 60 | 28 | — |

As can be seen from Table 3, in Example 3 in which irradiation with infrared radiation of 1,650 to 1,750 cm$^{-1}$ having a peak at 1,700 cm$^{-1}$ was performed, water was selectively vaporized under the irradiation.

Example 4

A flask equipped with a cooling tube and containing 25 mL of ethanol (99.5%) (manufactured by KANTO CHEMICAL Co., Inc.) was charged with 0.042 mol of 1,4-dibromobenzene (10.0 g: manufactured by TOKYO CHEMICAL INDUSTRY Co., Ltd.) and 0.042 mol of p-aminobenzoic acid (5.8 g: manufactured by TOKYO CHEMICAL INDUSTRY Co., Ltd.), and the mixture was heated to 60° C. to dissolve the reagents added. Next, the solution was filtered to remove impurities in the solution. Then the filtrate was irradiated with infrared radiation of 6 to 6.5 µm having a peak at 6.25 µm (5 W, area irradiated with infrared radiation: 3 cm square/irradiation energy per unit area: about 0.5 W/cm$^2$) through an upper opening of the flask. While the irradiation was continued, the filtrate was left to stand in a room at 23° C., and crystals were found to precipitate. The wavelength range of the infrared radiation used for irradiation corresponds to a wavelength range in which C=C stretching vibrations of the aromatic ring of p-aminobenzoic acid and C=O stretching vibrations of carboxy group in p-aminobenzoic acid occur.

Comparative Example 3

A flask equipped with a cooling tube and containing 25 mL of ethanol (99.5%) (manufactured by KANTO CHEMICAL Co., Inc.) was charged with 0.042 mol of 1,4-dibromobenzene (10.0 g: manufactured by TOKYO CHEMICAL INDUSTRY Co., Ltd.) and 0.042 mol of p-aminobenzoic acid (5.8 g: manufactured by TOKYO CHEMICAL INDUSTRY Co., Ltd.), and the mixture was heated to 60° C. to dissolve the reagents added. Next, the solution was filtered to remove impurities in the solution. The filtrate was left to stand in a room at 23° C., and crystals were found to precipitate.

The crystals precipitated in Example 4 and Comparative Example 3 were collected, washed with cold ethanol (4° C.), pure water (4° C.), and then cold ethanol (4° C.), and dried. Each sample was subjected to NMR measurement, and the molar percentage of 1,4-dibromobenzene and the molar percentage of p-aminobenzoic acid in the precipitated crystals were computed from the results of the integral ratio of signals in the spectrum. The results are shown in Table 4.

TABLE 4

| | Precipitated crystal (mol %) | |
| --- | --- | --- |
| | 1,4-dibromobenzene | p-aminobenzoic acid |
| Example 4 | 88 | 11 |
| Comparative Example 3 | 59 | 30 |

In Example 4, irradiation with infrared radiation of 6 to 6.5 µm having a peak at 6.25 µm was performed. In Comparative Example 3, irradiation with infrared radiation was not performed. As can be seen from Table 4, a larger amount of 1,4-dibromobenzene can be selectively recrystallized in Example 4. The results show that, under irradiation with the infrared radiation of 6 to 6.5 µm, absorption specific to p-aminobenzoic acid occurs and recrystallization of p-aminobenzoic acid is suppressed, so that 1,4-dibromobenzene can be crystallized preferentially.

It is needless to say that the present invention is not limited to the above-described examples, and that the present invention can be implemented in other various examples insofar as falling within the technical scope of the invention.

The present application claims priority from Japanese Patent Application No. 2016-161435 filed on Aug. 19, 2016, the entire contents of which are incorporated herein by reference.

What is claimed is:

1. An organic compound refinement method for refining a specific organic compound which is a target compound from at least two types of organic compounds, the method comprising separating the target compound from an organic compound other than the target compound while the at least two types of organic compounds are irradiated with light at an infrared absorption wavelength of a specific functional group that is not contained in the target compound but is contained in the organic compound other than the target compound, or separating the target compound from an organic compound other than the target compound while the at least two types of organic compounds are irradiated with light at an infrared absorption wavelength of a specific functional group that is contained in the target compound but is not contained in the organic compound other than the target compound, wherein the light at the infrared absorption wavelength of the specific functional group is set within a wavelength range of from 2.5 µm to 25 µm inclusive, and a half-width of a maximum peak of the irradiated infrared light is 1.5 µm or less.

2. The organic compound refinement method according to claim 1, wherein, during the irradiation with the light at the infrared absorption wavelength of the specific functional group, an infrared heater that emits, from a structural member thereof, the light at the infrared absorption wavelength of the specific functional group is used, the structural member including a metal pattern, a dielectric layer, and a metal substrate that are stacked in this order from an outer side toward an inner side.

3. The organic compound refinement method according to claim 2, wherein the metal pattern includes metal electrodes having the same shape and the same size and arranged on the dielectric layer at regular intervals, and wherein the peak wavelength of infrared radiation emitted from the infrared heater varies with a width of the metal electrodes.

4. An organic compound refinement method for refining a specific organic compound which is a target compound from at least two types of organic compounds, the method comprising separating the target compound from an organic compound other than the target compound while the at least two types of organic compounds are irradiated with light at an infrared absorption wavelength of a specific functional group that is not contained in the target compound but is contained in the organic compound other than the target compound, or separating the target compound from an organic compound other than the target compound while the at least two types of organic compounds are irradiated with light at an infrared absorption wavelength of a specific functional group that is contained in the target compound but is not contained in the organic compound other than the target compound, wherein, during the irradiation with the light at the infrared absorption wavelength of the specific functional group, a planar heater is used as an infrared heater that emits the light at the infrared absorption wavelength of the specific functional group.

5. The organic compound refinement method according to claim 4, wherein the light at the infrared absorption wavelength of the specific functional group is set within a wavelength range of from 2.5 μm to 25 μm inclusive.

6. The organic compound refinement method according to claim 4, wherein a half-width of a maximum peak of the irradiated infrared light is 1.5 μm or less.

7. The organic compound refinement method according to claim 1, wherein, during the irradiation with the light at the infrared absorption wavelength of the specific functional group, an infrared heater comprising a heating element and a plate-shaped member disposed below the heating element is used to emit the light at the infrared absorption wavelength of the specific functional group.

* * * * *